(12) United States Patent
Yi et al.

(10) Patent No.: US 7,609,810 B2
(45) Date of Patent: Oct. 27, 2009

(54) TREATMENT-SPEED REGULATED TUMOR-TRACKING

(76) Inventors: Byong Yong Yi, 3544 Lowlen Ct., Ellicott City, MD (US) 21042; Xinsheng Cedric Yu, 12707 Chapel Chase Dr., Clarksville, MD (US) 21029; Fritz Lerma, 1010 Concordia Dr., Towson, MD (US) 21286

( * ) Notice: Subject to any disclaimer, the term of this patent is extended or adjusted under 35 U.S.C. 154(b) by 123 days.

(21) Appl. No.: 11/956,697

(22) Filed: Dec. 14, 2007

(65) Prior Publication Data

US 2008/0144772 A1 Jun. 19, 2008

Related U.S. Application Data

(60) Provisional application No. 60/874,678, filed on Dec. 14, 2006.

(51) Int. Cl.
*A61N 5/10* (2006.01)
(52) U.S. Cl. ...................................... 378/65
(58) Field of Classification Search .............. 378/8, 378/20, 65, 95
See application file for complete search history.

(56) References Cited

U.S. PATENT DOCUMENTS

| | | | | |
|---|---|---|---|---|
| 5,538,494 | A * | 7/1996 | Matsuda | 600/1 |
| 5,764,723 | A * | 6/1998 | Weinberger et al. | 378/65 |
| 6,076,005 | A * | 6/2000 | Sontag et al. | 600/413 |
| 6,690,965 | B1 * | 2/2004 | Riaziat et al. | 600/428 |
| 6,804,548 | B2 * | 10/2004 | Takahashi et al. | 600/427 |
| 7,349,522 | B2 * | 3/2008 | Yan et al. | 378/65 |
| 7,412,029 | B2 * | 8/2008 | Myles | 378/65 |
| 7,453,983 | B2 * | 11/2008 | Schildkraut et al. | 378/65 |
| 7,453,984 | B2 * | 11/2008 | Chen et al. | 378/65 |
| 7,469,035 | B2 * | 12/2008 | Keall et al. | 378/65 |

\* cited by examiner

*Primary Examiner*—Allen C. Ho
(74) *Attorney, Agent, or Firm*—Gianna J. Arnold; Miles & Stockbridge P.C.

(57) ABSTRACT

A method for delivering therapeutic radiation to a tumor within a patient including: monitoring tumor motion in a preliminary procedure to generate and record a surrogate signal representing the tumor motion; determining a radiation therapy plan for the patient including a planned sequence of varying parameters of a radiation beam to track the tumor motion and a planned rate of execution of the planned sequence; configuring a radiation therapy device to deliver radiation in accordance with the radiation therapy plan, positioning the patient within the device, and activating the device to perform the planned sequence; monitoring tumor motion during the procedure to provide a treatment surrogate signal; determining the difference between the estimated and treatment surrogate signals; and regulating the speed of the radiation treatment procedure by varying the rate of execution of the sequence of beam parameters in accordance with the difference between the estimated and treatment surrogate signals.

23 Claims, 8 Drawing Sheets

TREATMENT-SPEED REGULATED TUMOR-TRACKING

CROSS-REFERENCE TO RELATED APPLICATIONS

This application claims the benefit of U.S. provisional patent application No. 60/874,678, filed on Dec. 14, 2006, the entire disclosure of which is incorporated herein by reference.

BACKGROUND OF THE INVENTION

1. Field of the Invention

The present invention relates to methods and systems for the planning and delivery of radiation therapy. In particular, the invention relates to methods and systems for real-time tumor tracking with a preprogrammed delivery sequence and adaptive treatment speed modulation to account for tumor motion caused by breathing.

2. Description of Related Art

Radiation therapy is used to treat cancers and other conditions in patients. One commonly used form of radiation therapy is external beam radiation therapy. In external beam radiation therapy, a high energy x-ray beam generated by a machine (usually a linear accelerator) or a charged particle beam, generated by a particle accelerator, (herein, an accelerator means either an x-ray linear accelerator or a particle accelerator for description convenience) located outside of the patient's body is directed at a tumor or cancerous cells inside the patient's body. While the radiation kills the cancerous cells it also harms normal tissue and organs in the vicinity of the tumor/cancerous cells in the patient. Thus, a goal in radiation therapy is to deliver the required dose of radiation to the smallest possible target volume to minimize the radiation dose that may impact surrounding normal tissue.

There are several sources of error that are encountered in radiation therapy. First, there is error involved in delineating the boundaries of the target (as used herein, "target" refers to the area in which the delivery of radiation is desired such as a tumor). Second, there is error due to target motion. Target motion refers to motion of a target due to patient bodily functions, during irradiation and between treatment sessions. For example, breathing will cause motion in the organs located in the thorax and abdomen of a patient, during the treatment. This motion can take the form of translation of the target (e.g., a patient's liver moves up and down as the patient breathes while lying on a treatment table) and/or changes in the shape and size of the target (e.g., a patient's lungs expand, contract and distort during breathing). Finally, there is error due to set up of the patient relative to the radiotherapy machine (e.g., errors in directing the beam toward the patient, etc.). This disclosure is primarily directed toward the second source of error, target motion.

One method for dealing with error due to target motion is to increase the treatment volume (the difference between the treatment volume and a diseased area for which radiation treatment is desired is sometimes referred to as margin) so that the treatment volume is large enough to include the entire range of motion through which the target will travel during the radiation treatment. This approach, however, results in radiation being delivered to normal tissue inside the treatment volume (e.g., normal tissue will be present at the "bottom" of the treatment volume when the target is at the "top" of the treatment volume) and is therefore not desirable.

Another method uses a device to hold a patient's breathing, or requires the patient to hold their breath when the radiation beam is turned on. However, the duty cycles of such systems are low. "Duty cycle" is defined as the percentage of time the beam is on from start to end of each beam delivery, where 100% duty cycle implies no beam interruptions. This scheme also leads to patient discomfort. Moreover, such a scheme is not feasible for patients with certain illnesses such as lung cancer, or patients otherwise having compromised lung functions. This technique is also time consuming in that the period of time for which a patient can hold his or her breath is limited and the delivery of radiation is halted when the patient does not hold his or her breath. Moreover, this technique requires the patient to hold his or her breath at a desired point, and the patient may not be able to hold his or her breath at the desired point accurately.

Another method that has been utilized to reduce error due to target motion is "gating." In this method, the therapy beam aperture is reduced, to focus on a discrete, pre-selected position of the target at a particular time window during the patient's breathing cycle. It is assumed that the target motion correlates with the breathing cycle, such that the tumor will return to the treatment position at the same time window of the breathing cycle, during the entire course of therapy. A sensor monitors a patient's breath or abdominal excursion (during breathing) and triggers the delivery of a pulse of radiation at the pre-selected time window. The time window may be selected when the patient's lungs are nearly full as the patient inhales (or, alternatively, when the patient's lungs are nearly empty as the patient exhales). This technique is less than optimal as it is time consuming because the radiation is delivered during only a portion (typically 30%-40% time window) of a patient's breath cycle (the duty cycle of such systems is low). In the gating method, the tumor also moves within the time window, although much less than its full range of motion. Therefore, a margin, or a residual margin, is also required to ensure that the tumor gets the intended dose of radiation.

A fourth method that has been explored for reducing error due to target motion is target tracking. In target tracking techniques, the radiation beam follows motion of the target. Three different tracking techniques are presently proposed or implemented. The first tracking technique is achieved by moving the entire treatment head to track the tumor motion, using a robotic arm that carries the accelerator around the patient during the radiation beam delivery. This technique can adjust to changes in patient breathing patterns, but it is impossible for non-robotic, commercially available linear accelerator systems, to emulate such method. Notably, only a small fraction of all linear accelerators or external beam radiation equipment has such robotic capability, and widespread use is expected to be limited. A second tumor tracking technique uses a stationary accelerator equipped with a multi-leaf collimator (MLC), which moves the radiation beam dynamically to track target motions in real time. Dynamically tracking the target minimizes the effects of intra-treatment organ motion, and thereby reduces the margin typically assigned around a moving tumor. Unlike gating, the treatment delivery is not interrupted, and thus is intended to maintain high treatment efficiency. Tracking the tumor with MLC motion also has the advantage of distributing the normal tissue dose over a greater volume, thus lowering the dose burden to the skin and underlying structures. Previous techniques proposed to control the MLC motion to track the tumor along with a program are (1) motion-adaptive x-ray therapy (MAX-T), (2) synchronized moving-aperture radiation therapy (SMART), and (3) aperture maneuver with compelled breath (AMC). Because the motion caused by breathing is more or less cyclical, one can program the MLC to move repeating a pre-defined cycle, assuming that the frequency and amplitude of the motion are correct. But in fact, the motion is not truly following a fixed cycle, instead, there are significant variations in frequency and amplitude between patients and for the same patient at different times (particularly in the high-stress situation that pertains when he or she is undergoing treatment). Accurate tracking of tumor motion with programmed MLC motion sequences requires that the patient's breathing pattern be perfectly consistent with that used for planning. It is well known that patients do not breathe consistently and reproducibly. Significant changes in breathing patterns have been observed within a single breathing session and between different breathing sessions. These irregularities in patient breathing have limited the efficiency of these techniques, leading to the suggestion of combining aperture motion with some kind of patient breath control, thus introducing additional difficulties. Neither MAX-T nor SMART includes an effective method to compensate for irregular breathing, and AMC relies on the patient's active cooperation. MAX-T requires constantly detecting the target position, predicting where it is going, and directing the MLC or treatment table to move; SMART requires the patient to follow a breathing cycle exactly as seen during planning and thus SMART and AMC cannot function in the presence of involuntary patient bodily, or breathing motion. Thus, MAX-T requires real-time feedback control, and for SMART and AMC it is technically challenging to track a tumor solely based on the patient's cooperation, and thus these techniques are further impractical. In order to deliver SMART or AMC, audio and/or video instructions are available to guide the patient to breathe in a consistent pattern. However, such approach has limited applicability, because most patients, especially lung cancer patients, are incapable of breathing without many irregularities; even when they attempt to do so, they most often fail to follow audio or video breathing guidance cues. Although such a pitfall is not present in MAX-T, MAX-T requires a modification of leaf positions in real time, a feature that is not feasible with commercially available MLC systems. In addition to the technical difficulties, real-time modification or creation of a treatment sequence can also raise issues of reliability and safety (for example, the chance for error in calculations performed in real time increases). As a result, no dynamic tracking has been implemented clinically.

In summary, a target tracking method may be used for reducing error due to target motion. In target tracking techniques, the radiation beam follows the motion of the target. However, target motion cannot be accurately predicted. One tracking technique utilizes tracking with guided breathing that requires a patient to follow a breathing pattern to match motion of a radiation beam that is preprogrammed according to the guided breathing pattern. This scheme has problems in that there are some patients that may be incapable of following audio or video breathing guidance cues in spite of extensive training. In another proposed tracking technique, target motion is tracked in real-time and the radiation beam is moved in real time in accordance with the detected motion. This technique is difficult to implement, as the calculations necessary to control movement of the beam are difficult to perform in real time and the MLCs or patient supporting assembly, or table, cannot reach the commanded location quickly. This technique also presents a safety issue as the chance for error in calculations performed in real time increases. Thus, there is a need for a safe and effective method of reducing error due to target motion that circumvents the technical challenges in MLC-based tumor tracking

SUMMARY OF THE INVENTION

This disclosure introduces a new approach, named Treatment Speed Regulated Tumor Tracking (i.e., TSR Tracking). TSR Tracking commands a stationary or rotating linear accelerator equipped with an MLC, or a particle accelerator, to track the tumor motion. TSR Tracking considers the tumor motion during the treatment planning process and handles only the irregularity of tumor motion during the delivery of each treatment. Thus, TSR Tracking achieves tumor tracking in two steps: 1) creating a plan to irradiate a tumor, as a function of a patient's breathing or as a function of the motion of the tumor, and 2) regulating the speed of delivery according to irregularities in the patient's breathing or irregularities in the motion of the tumor during the delivery of the treatment. This is unlike the MAX-T tracking approach described above, in which a radiotherapy plan assumes the tumor is stationary and target motion is handled completely at the time of delivery. TSR Tracking is different from the SMART and AMC tracking methods described above, which require the patient to follow a planned breathing motion, because TSR Tracking adjusts the pace of delivery to follow the patient's breathing.

Multiple issues in tracking tumor motion during radiation delivery with external beam radiotherapy have been identified above, and can be summarized to include the need for large robotic accelerator translation hardware, new MLC design to rapidly move to a new un-planned position, new hardware to shift a treatment table during beam delivery, or need for a patient to follow a strict breathing sequence, which cannot be achieved even with breath training and guidance. These issues are addressed by the method and system presented herein, referred to as TSR Tracking radiotherapy. The TSR Tracking method and system corrects for deviations in patient breathing patterns and do not require significant hardware modifications, but rather intentional plan design and control of delivery speed. Thus, TSR Tracking is designed to effectively achieve real-time adaptive tumor tracking with preprogrammed treatment parameters, and is realizable with a variety of treatment unit designs. Thus, this system separates the task of tumor tracking into two components: 1) tumor motion as a function of patient breathing and 2) patient breathing irregularity. Rather than considering the tumor as stationary at planning time and handling both components of tracking completely at the delivery time as with other tracking methods, TSR Tracking handles the first component at the planning time and the second component at the delivery time. The tumor moves partly as a function of breathing and TSR Tracking can plan for this using a preprogrammed MLC movement sequence designed to track an expected, regular tumor motion trajectory, and associated tumor shape changes. Subsequently, at the time of delivery TSR Tracking regulates the pace of treatment delivery to follow the breathing speed of the patient. TSR Tracking methods and systems do not require real-time recalculation of movement parameters in a treatment plan; do not require patients to adhere to a predetermined breathing pattern in order to receive treatment; and do not require novel hardware design that challenges mechanical operation limits of MLC systems or treatment table design. TSR Tracking delivers efficient tumor-tracking treatments via a system that can operate with approximately 100% duty cycle, thus nearly eliminating interruptions in irradiation during the treatment delivery.

Because TSR Tracking plans for target motion, TSR Tracking requires that the target's shape and location, as a function of breathing signal or an implanted marker motion signal, is known at the time of planning. The words "breathing signal" here can mean the tidal volume, chest wall expansion, the temperature fluctuations around the mouth and the nose, the diaphragm position or any other physical characteristics associated with breathing including the tumor location itself as may be measured with an implanted marker. No matter how breathing is measured, the first task of planning TSR Tracking treatment is to establish a one-to-one relationship between the measured breathing signal, as a surrogate of patient's breathing, and the target's location and shape. Such relationship is commonly obtained with four-dimensional (4D) CT or MR imaging, which provides multiple three-dimensional images of the patient, each representing the patient's anatomy at a known segment of the patient's breathing cycle. In the context of imaging and planning in radiation therapy, 4D implies spatial information in three dimensions as a function of time, where time is the fourth dimension. This one-to-one relationship, together with the computed average breathing frequency for the specific patient, allows the planning system to generate a dynamic treatment plan that delivers the required radiation doses to the target while sparing the surrounding normal structures. Unlike the other tumor tracking schemes, which model the patient as a 3D object during planning, the treatment planning process for TSR Tracking is 4D by nature and is capable of tracking the tumor motion perfectly if the patient breathes the same way as he/she did during 4D imaging.

The breathing signal of the patient is monitored during the actual delivery of radiation. "Treatment delivery" represents all variables of a treatment, including the radiation dose, the movement of the MLC apertures, and the movement of treatment couch, collimator and machine gantry. All modern radiation treatment machines are designed to maintain the synchrony of a set of different treatment variables so that a desired treatment sequence can be delivered accurately. One of these variables may be used as the main axis, or variable, of delivery while the rest are dependent variables made to vary with the main variable under the central control of the machine controller. The speed of the pre-programmed movements of the radiation beam can be altered by changing the speed of execution of the variable used by the machine as its main treatment delivery axis. For example, most linear accelerators deliver radiation treatments by slaving the other aspects of delivery, such as MLC motion, to the delivered dose measured by machine monitor units. Therefore, increasing the machine dose rate will speed-up the preprogrammed MLC motion, and vice versa. TSR Tracking exploits this character, by deliberately changing the dose rate or any other variable used as the main axis of treatment delivery to alter the rate of execution of the planned delivery sequence. Thus, TSR Tracking effectively enables the treatment delivery to follow the patient's irregular breathing, rather than asking the patient to follow a predetermined breathing pattern. In TSR Tracking, the relative movements between the patient and the radiation beam are not modified; rather, by modifying the dose rate or other parameter used by the accelerator as the main axis of delivery, the speed at which the pre-programmed movements occur is modified.

As described above, for most linear accelerators, delivered dose is used as the main axis (or lead variable) of radiation delivery. By altering the dose rate during beam delivery, a global change can be introduced in treatment speed, causing changes in the speed of the MLC's motion, gantry movements, collimator movements or table movements. In this embodiment, the dose rate may be regulated in several different ways. In one embodiment, the delivery of radiation by the radiation therapy device is controlled by a pulsed signal, and the pulse repetition rate and/or the pulse width of the pulsed signal is regulated to regulate the dose rate. In another embodiment, an attenuation material (e.g., a lead shield) is selectively interposed between the source of the radiation beam and the patient to regulate the dose rate. In still other embodiments, a signal that controls the delivery of radiation by the radiation therapy device is selectively gated or switched on and off to regulate the dose rate.

The present invention overcomes a major obstacle in the field of radiation therapy by providing safe and effective methods and systems for real-time closed-loop tracking with a preprogrammed delivery sequence and adaptive treatment speed regulation to account for breathing irregularities. The methods enable tumor tracking even for irregular breathing with amplitude and frequency variations without requiring significant modification of the existing treatment machine.

There has thus been outlined, rather broadly, the more important features of the invention in order that the detailed description thereof that follows may be better understood, and in order that the present contribution to the art may be better appreciated. There are, of course, additional features of the invention that will be described further hereinafter. Indeed, it is to be understood that both the foregoing general description and the following detailed description are exemplary and explanatory and are intended to provide further explanation of the invention as claimed.

In this respect, before explaining at least one embodiment of the invention in detail, it is to be understood that the invention is not limited in its application to the details of construction and to the arrangements of the components set forth in the following description, figures, or drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods, and systems for carrying out the several purposes of the present invention. It is important, therefore, that equivalent constructions insofar as they do not depart from the spirit and scope of the present invention, are included in the present invention.

The accompanying drawings are included to provide a further understanding of the invention and are incorporated in and constitute a part of this specification, illustrate several embodiments of the invention and together with the description serve to explain the principles of the invention.

BRIEF DESCRIPTION OF THE DRAWINGS

FIG. 7A depicts a desired intensity pattern delivered to a film placed in a stationary phantom.

FIG. 7B depicts the same intended intensity pattern delivered to a film in a moving phantom which keeps changing its frequency irregularly.

FIG. 7C depicts the same delivery as in FIG. 7B delivered to a film in the irregularly moving phantom after employing the TSR Tracking strategy.

DETAILED DESCRIPTION OF THE INVENTION

Figure 1:
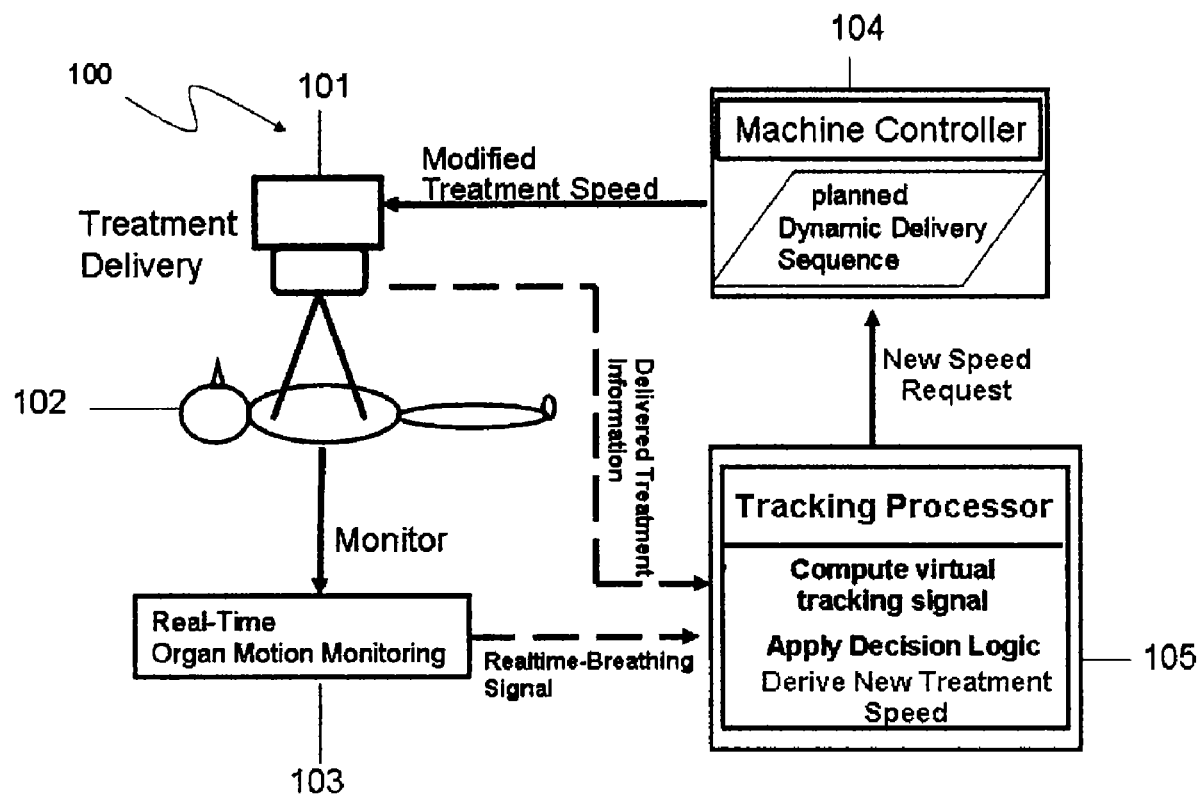
FIG. 1 illustrates an exemplary TSR Tracking system for regulating a radiation dose rate supplied to a patient.

TSR Tracking, a new tumor-tracking method, is disclosed herein. In TSR Tracking, a dynamic treatment sequence is planned to irradiate a known moving target as a function of a predetermined breathing signal. The speed at which this dynamic treatment sequence is delivered is altered in real-time according to the difference of the breathing signal measured in real-time and the breathing signal used for planning the treatment sequence. According to this invention the movement of the tumor is tracked, and real-time changes in tumor motion patterns are accommodated so that the target margin around the tumor can be minimized to reduce the toxicity to surrounding normal tissues/structures. Rather than designing the treatment plan assuming the target is stationary and tracking the tumor motion only at the time of treatment delivery, the method plans the treatment considering tumor motion and only handles the irregularities of tumor motion as the result of irregular breathing at the delivery time.

For moving targets, a 4D-imaging study with free breathing is performed. The resulting 4D images provide one-to-one correlation between the target shape and location and the breathing signal because the breathing signal and the patient anatomy are acquired simultaneously during 4D imaging. "Breathing signal" is broadly defined as any direct or indirect measurement of the breathing itself or the effect of breathing as a function of time. This correlation allows the treatment planning system to generate a treatment plan that will track the movement of the target during treatment. In one embodiment using a linear accelerator, the movement of the radiation beam as a function of delivered radiation monitor units is achieved by a multileaf collimator (MLC).

The breathing signal of the patient at the time of treatment can differ from that monitored during the free-breathing 4D imaging study and thus is monitored during the delivery of radiation. The breathing signal used for planning and that acquired at the time of delivery could differ in two aspects: the length of the breathing cycle and the amplitude or depth of breathing. The programmed movement of the radiation beam for tracking the target is based on the average breathing signal at the time of the 4D imaging study. If the delivery of this planned treatment is deliberately slowed down, it is equivalent to the delivery of a treatment that has been planned by using a 4D scan and breathing signal acquired at a slower breathing rate, and vice versa. When the treatment is slowed down, the breathing signal used in planning, which is played back during treatment delivery, is consequently adjusted. The equivalent, or resultant, breathing signal corresponding to the altered treatment speed is called the virtual tracking signal, or simply, tracking signal. The goal of TSR Tracking at the time of delivery is to modify the treatment delivery speed such that the difference between the corresponding tracking signal and the patient's actual breathing signal being acquired in real-time is minimized.

According to the TSR Tracking strategy, to compensate for breathing frequency differences between the tracking signal and the real-time breathing signal, the pre-programmed delivery may be accelerated or decelerated. When the patient's breathing frequency on the treatment day is higher than that used for programming the delivery sequence, the treatment speed needs to be increased. The treatment speed needs to be decreased in order to track the tumor when the patient's breathing frequency on the treatment day is lower. Breathing phase shifts also can be corrected by adjusting the treatment speed in the same manner. If the tracking signal is behind the breathing signal acquired at the time, the treatment speed needs to be increased. Conversely, if the tracking signal is ahead of the real-time breathing signal, the treatment speed should be decreased. When the patient's breathing amplitude is higher than that used for programming the delivery, the beam needs to be halted until the amplitude of the real-time breathing signal comes back to the range of the tracking signal. When the amplitude of the real-time breathing signal is lower, the treatment speed needs to be increased to the maximum (for a short duration) to minimize the error due to this amplitude variation.

TSR Tracking can be embodied by dose rate regulation. The embodiments described below are methods and systems for regulating the radiation dose supplied to a patient receiving treatment and for achieving a significant reduction in unwanted dose to the patient by reducing the margins. In order to explain the principle of the idea, "dose rate" means the treatment speed. Hence, "dose rate regulated tracking" or "DRRT," which is explained below, will have the same meaning as TSR Tracking. FIG. 1 illustrates an exemplary TSR Tracking system 100 for regulating a radiation dose rate supplied to a patient. Such a TSR Tracking system 100 includes a breathing monitoring unit 103 that is the same unit used for obtaining the breathing signal for planning the dynamic delivery sequence. The planned dynamic delivery sequence is uploaded and stored in the radiation delivery machine controller 104. Based on the real-time breathing signal acquired by the breathing monitoring unit 103, and the information on the actual treatment delivery, the tracking processor 105, computes the tracking signal corresponding to the delivery and compares the tracking signal with the real-time breathing signal. A new treatment speed is derived by the tracking processor 105 and is sent to the machine controller 104. The radiation therapy machine 101 then adjusts the treatment speed to synchronize the delivery of the planned sequence with the patient's breathing. Thereafter, the treatment speed of the radiation therapy device is regulated in accordance with the difference between the tracking signal and the real-time breathing signal. Regulation of the treatment speed causes the pre-planned movement of the radiation beam to vary so as to remain synchronous with the actual breathing pattern of the patient.

Figure 2:
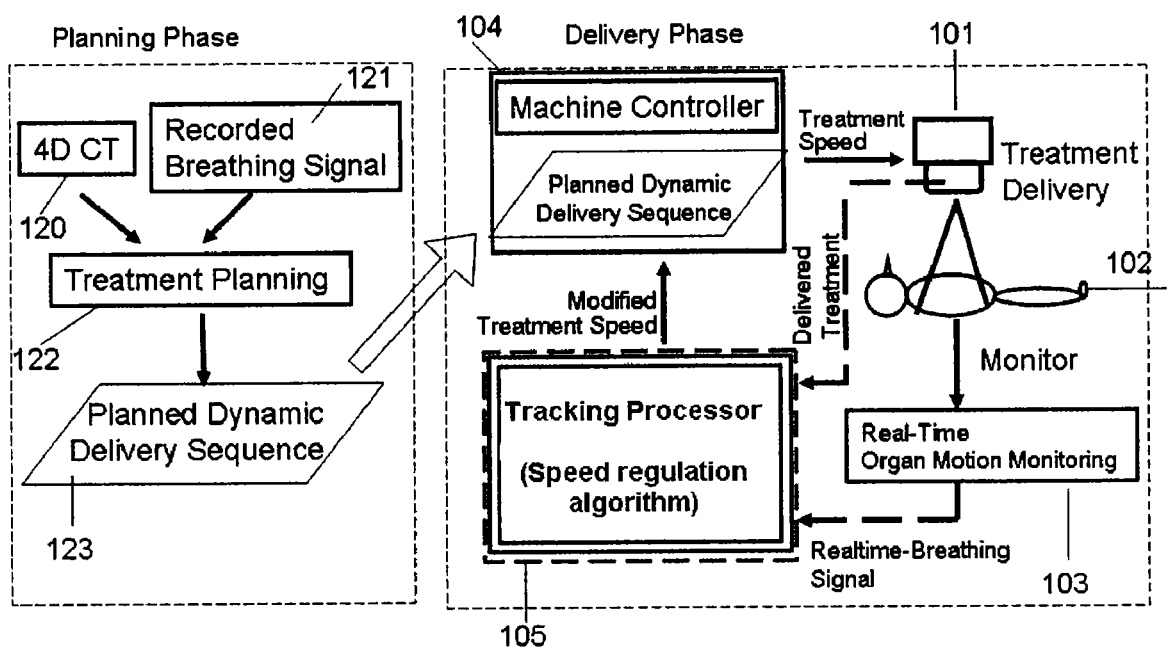
FIG. 2 illustrates an exemplary conceptual system diagram of an embodiment for implementing the TSR Tracking system.

FIG. 2 illustrates an exemplary conceptual system diagram of another embodiment 100 of a TSR Tracking system. The TSR Tracking scheme consists of two phases: the planning phase and the delivery phase. This embodiment of planning phase includes a four-dimensional computed tomography device 120 (4D CT). 4D CT 120 enables the study of the human body through the imaging of cross-sectional slices of the patient's anatomy in three dimensions as a function of time, where time is the fourth dimension. An X-ray technique may be used in 4D CT 120 in order to produce a detailed cross-section of a tissue structure at a predetermined depth. With 4D CT 120, a medical professional is able to produce snapshots of, for example, the abdomen of a patient where the tumor or organ target may reside. Further, the 4D CT 120 provides multiple images that correspond to different points in the breathing cycle of the patient. Thus, using these images, the location of a target at different points in a patient's breathing cycle can be determined. The information acquired from 4D CT 120 together with the recorded breathing signal are input to the computer planning system 122 in order to develop a computerized treatment plan. Using the target location information from the images from 4D CT 120 and the recorded breathing signal from 121, the correlation between the target motion and the breathing signal is established by the computer planning module 122, which then derives a dynamic delivery sequence 123 to track the tumor if the patient breathes the same way during treatment delivery. This planned dynamic delivery sequence is loaded to the radiation treatment machine controller 104. The dynamic delivery sequence specifies all parameters or variables of a treatment delivery including the positions of MLC leaves, collimator angle, field size, gantry angle, and table position. The treatment machine 101 delivers radiation beams to a patient 102. After the patient is set up for treatment, the breathing monitoring unit will be activated to provide the real-time breathing signal to the tracking processor 105. The tracking processor 105 is also connected to the treatment machine controller 104, through which the radiation will be turned on at the planned point of the breathing cycle. In operation, the target motion monitoring device 103 generates a real-time breathing signal that is continuously compared with the tracking signal, which is a virtual signal corresponding to the actual treatment delivery. The tracking processor 105 applies a tracking algorithm and control logic to alter the speed to treatment delivery through the machine controller 104. Therefore, by regulating the treatment speed via the tracking processor 105, which in turn serves as input to the machine controller 104, radiation treatment is delivered to a patient via a treatment delivery device 101 that accurately tracks motion of the target organ or tumor in real time.

FIG. 2 also shows an embodiment of delivery phase of a TSR Tracking system. On the day of treatment, however, the patient may not breathe according to the exact breathing pattern one acquired during the free-breathing imaging studies and used for generating the dynamic delivery sequence. Therefore, a real-time target motion monitoring device 103 is utilized to detect the actual breathing pattern as radiation treatment is being delivered. The motion monitoring device 103 generates a real-time breathing signal that serves as a feedback signal to the tracking processor 105, which regulates the treatment speed through machine controller 104 such that the pre-programmed delivery sequence remain synchronized to the breathing-induced target motion.

Dose rate is the one of the major components that changes the treatment speed. The embodiment of treatment speed change can be achieved by dose rate regulation. Dose rate regulation methods include, for example, switching, gating, adjusting the pulse repetition rate, and changing attenuation materials. The treatment tracking parameters may remain as a same function of monitor unit but may operate at a different function of time. As a result of the regulation of the dose rate being synchronized to the target motion, the radiation beam from the DRRT device tracks both regular and irregular motion of the target.

When a deviation between the virtual tracking signal and the actual breathing signal is detected, the computer that monitors patient breathing must generate a correction signal to the accelerator to increase or decrease the dose rate. The correction signal contains two values: 1) the dose rate, $d_r$, to which the machine must be increased for a short duration T'; and the dose rate, $d_s$, to which the machine must be returning to after the duration T'. T' is the time within which the user desires to achieve synchrony and it can be custom set to a reasonable value, for example, within 0.3 seconds. Therefore, $d_r$ is a temporary measure to make-up the difference with the desired time period T' and $d_s$ is a "stable state" dose rate determined based on the breathing parameters derived from the measured breathing pattern of the day up to this point. With this correction algorithm, the corrections are more frequent in the beginning of the treatment. As the treatment proceeds, the frequency of corrections needed to maintain synchrony will be significantly reduced. For machines that cannot precisely set $d_r$ and $d_s$, frequent correction will be needed during the whole treatment.

The dose rate may be regulated in several different ways. In one embodiment, the delivery of radiation by the radiation therapy device is controlled by a pulsed signal, and the pulse repetition rate and/or the pulse width of the pulsed signal is modified. Pulse repetition rate refers to the average number of pulses in unit time during a specified period. Therefore, by increasing or decreasing the pulse repetition rate of a control signal that controls the radiation therapy device, the dose rate of radiation delivered to the patient increases or decreases, respectively. Further, the pulse width of the control signal that controls the radiation therapy device may also be varied in order to regulate the dose rate of radiation delivered to a patient. As used herein, the pulse width of the control signal refers to the interval of device "ON" time in a period. Thus, by varying the pulse width of the control signal to the radiation therapy device, the dose rate of radiation delivered to a patient can be modified (for example, regulated). For example, the dose rate of radiation delivered to the patient increases and decreases in accordance with intervals of long and short pulse widths, respectively, of the control signal. In another embodiment, an attenuation material (such as a lead shield) is interposed between the source of the radiation beam and the patient. Lead shields are used when possible to shield radiosensitive organs from radiation that is delivered to a patient. Thus, by varying the masking of the target with a lead shield, the dose rate of radiation delivered to the target may be regulated.

Other parameters of the radiation therapy treatment may also be regulated in order to regulate the speed of treatment. For example, the delivery of radiation may be controlled by regulating the gantry speed by conventional apparatus and procedures such as mechanical or electrical sensors or breakers. Again, it is possible to regulate only the leaf positions of the multi-leaf collimator to adjust the dose rate during dynamic arc delivery. For the latter case, gantry angle deviation may be allowed within a preset tolerance range (for example, 5 degrees).

Furthermore, a charged particle beam may be delivered with an energy variation to access multiple penetration depths, wherein the rate at which the energy is delivered is regulated by generally conventional methods, e.g., using a series of electronic gating signals or by using a mechanical range modulator (RM) of the charged particle beams for modulating the treatment range.

Accordingly, a system for regulating the speed of radiation therapy treatment delivered to a patient, may comprise:

a detection mechanism for obtaining the time course of tumor motion (shape and location change) and its correlation with a measurable surrogate, typically a physical signal associated with breathing or the location of implanted markers in the tumor, for a patient in need of radiation therapy;

a determining mechanism for determining a radiation therapy plan for the patient, the radiation therapy plan including a target location that varies in accordance with the estimated breathing pattern;

a configuring mechanism for configuring a radiation therapy device to deliver radiation in accordance with the radiation therapy plan;

an activating mechanism for activating the radiation therapy device;

a monitoring mechanism for monitoring an actual breathing pattern of the patient during delivery of radiation;

a second determining mechanism for determining a difference between the estimated breathing pattern and the actual breathing pattern of the patient; and a regulating mechanism for regulating a treatment speed of the radiation therapy device in accordance with the difference.

In particular, in such a system the dose rate may be regulated by regulating the pulse rate or pulse width at which the radiation therapy device delivers pulses of radiation to the patient. The gantry speed may be regulated by any apparatus conventional in such systems, such as a mechanical breaker. Alternatively, only leaf positions of the multi-leaf collimator may be regulated by adjusting the dose rate during dynamic arc delivery. In such a case gantry angle deviations may be allowed within a preset tolerance range (for example, 5 degrees).

Furthermore, in such a system, the energy variation speed may be regulated by using a series of gating signals or by using pulse rate or pulse width signals to a mechanical range modulator (RM) or digital range modulator of the charged particle beams for modulating the treatment range.

Figure 3:
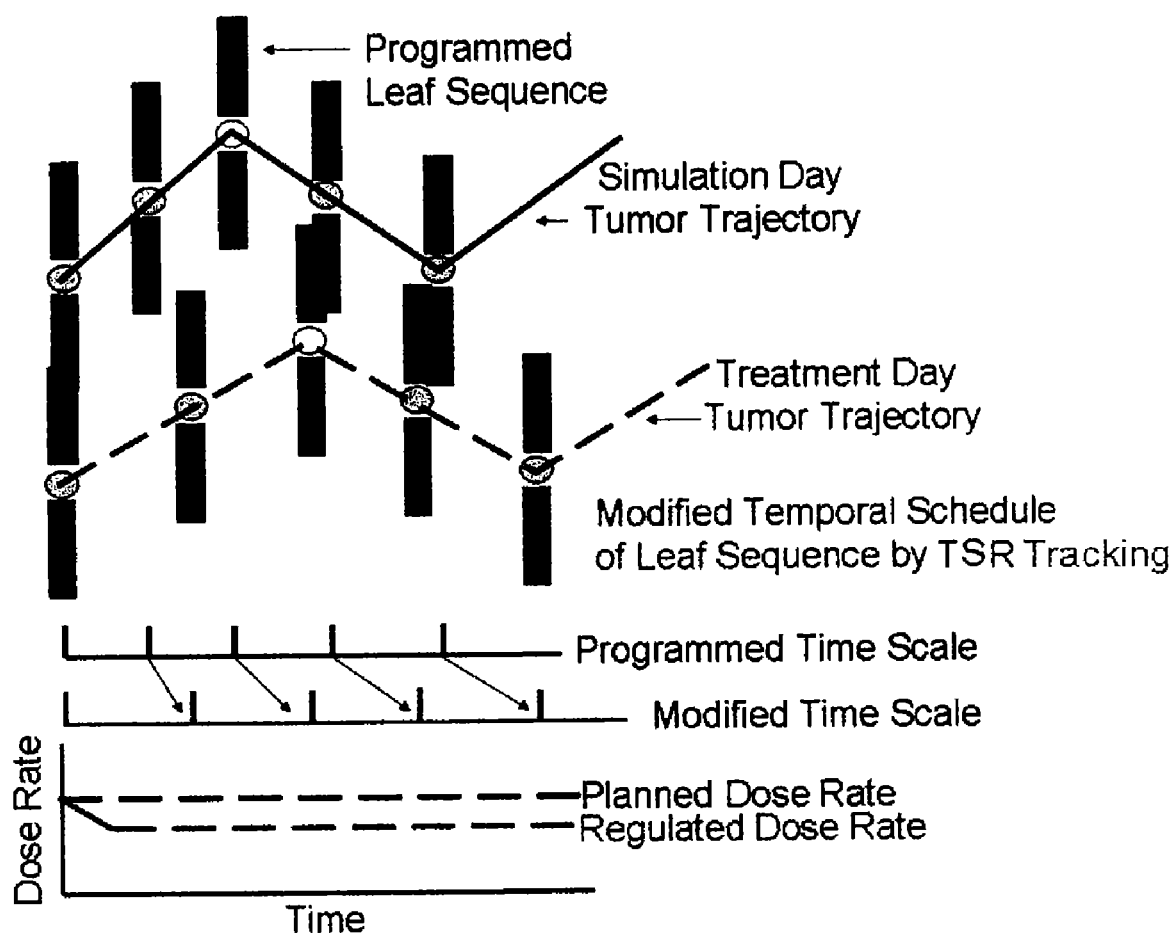
FIG. 3 illustrates an example of the principle of real-time feedback tracking with TSR Tracking (see "DRRT" below) by showing the temporal leaf positions and temporal dose rate variations that are needed to synchronize the MLC position with that of the tumor.

FIG. 3 illustrates an example of the principle of real-time feedback tracking with TSR Tracking by showing the temporal leaf positions and temporal dose rate variations that are needed to synchronize the MLC position with that of the tumor. The circles depicted between the MLC leaf openings illustrate the tumor locations as a function of time (horizontal axis). Based on the tumor motion trajectory on the day of imaging, a programmed leaf sequence tracks the tumor motion perfectly (illustrated at the top of FIG. 3). On the treatment day, the patient breathes slower, causing the tumor motion trajectory (circles connected by the dashed line) to differ from that on the day of imaging. If the treatment is delivered at the planned speed, the tumor will not be kept in the opening of the MLC. By reducing the dose rate, the movement of MLC is slowed down, thereby keeping the aperture between the MLC leaves surrounding the tumor. FIG. 3 further illustrates how the dose rate of an external beam radiation therapy unit is adaptively regulated in order to synchronize the dynamic treatment sequence and the motion of the tumor target. This feature helps minimize a potential treatment error that may occur due to an uncertainty resulting from an uncertainty generated from non-identical breathing between planning and treatment days. The movement of the tracking treatment sequence parameters (TTSPs) (including MLC parameters, gantry angles, collimator angles, treatment table coordinates, and field sizes) are slaved to (direct function of) the delivered monitor units. Monitor units (MU) represent an amount of radiation produced by the treatment machine.

Figure 4:
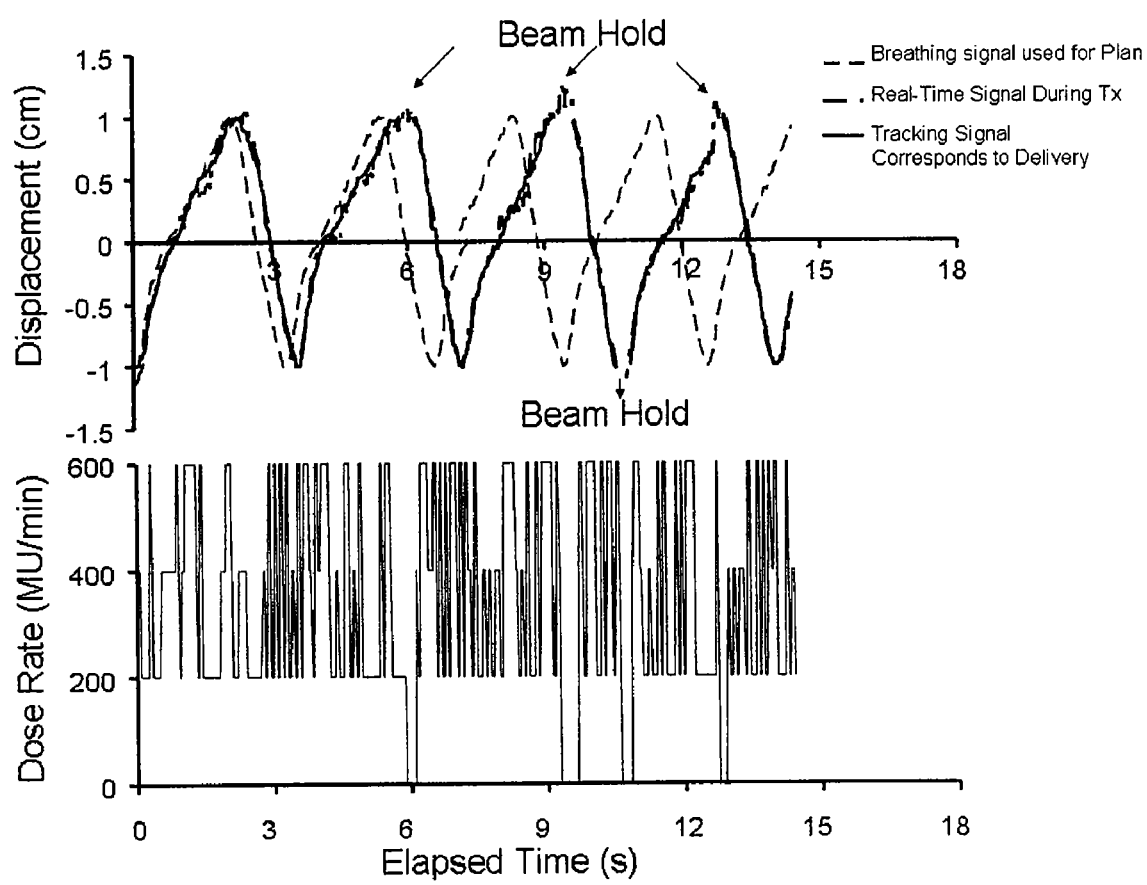
FIG. 4 shows an example of tracking results of using TSR Tracking to track tumor motion in real time with a preprogrammed dynamic treatment sequence.

FIG. 4 shows TSR Tracking by adjustment of dose rate. The top shows the comparison of the breathing signal used for planning, the real-time breathing signal, and the tracking signal corresponding to the actual treatment speed regulated by regulating the dose rate. The breathing signal used for planning, shown as a dashed line, is recorded during the 4D imaging session and used in planning the treatment. The real-time signal during treatment is the breathing signal of the patient as measured during the delivery of the treatment (and is shown as the highly fluctuating dash-dot line). The latter two signals are matched at the beginning of the graph. However, the real-time breathing signal in this example indicates the patient breathing slower and more irregularly during the treatment day. Using TSR Tracking, the treatment speed is adjusted by varying the machine dose rate, and the delivery of the treatment sequence is slowed down in general. As a result, the treatment delivery is equivalent to a dynamic treatment sequence created with a slower breathing pattern, shown as the virtual tracking signal (solid line). The bottom panel of FIG. 4 shows the dose rate during treatment delivery using TSR Tracking. The planned dose rate was 400 MU/min. During treatment delivery, the tracking processor makes constant adjustments to the dose rate based on the comparison between the real-time breathing signal and the virtual tracking signal. As a result, the difference between the real-time breathing signal and the tracking signal is very small. In this graph, there are four instances where the real-time signal during treatment is significantly deeper than the breathing signal obtained during imaging. In such instances, a weak correlation is expected between the real-time tumor location and the tumor location as seen in imaging. Therefore, it is expected that at such deeper breathing the planned treatment apertures would miss the tumor. To correct for these extreme variations, TSR Tracking interrupts the radiation beam briefly, until the amplitude of the real-time signal is returned to the planned range, as indicated in the figure. The adjustments in dose rate as calculated in TSR Tracking are indicated in the lower graph, where the dose rate in this example is adjusted between 200 and 600 MU/min several times per second. Notably, the four brief beam holds calculated by TSR Tracking are shown near 6, 9, 11, and 13 seconds with a Dose Rate of 0 MU/min The dose rate adjustment can be in discrete steps or continuous.

Figure 5:
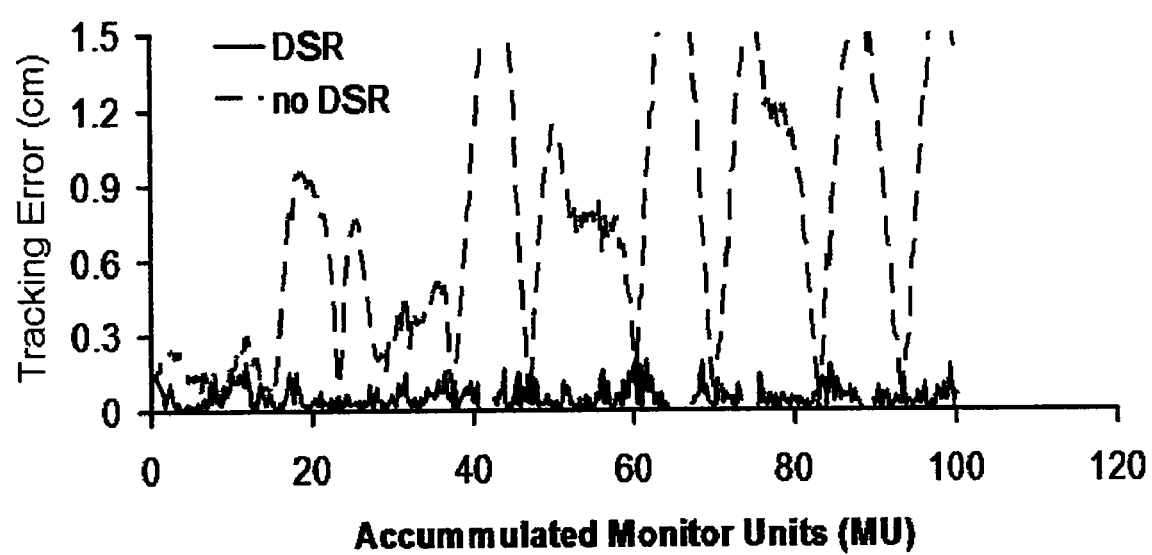
FIG. 5 shows the tracking error (residual motion) of the tracking depicted in FIG. 4.

FIG. 5 shows the tracking error (residual motion) of the tracking depicted in FIG. 4. An accuracy of better than 2 mm is achieved with TSR Tracking, while significant errors exceeding 1.5 cm can occur without TSR Tracking.

In operation, when a patient's actual breathing is ahead of the estimated breathing, the dose rate may be decreased. When the patient's actual breathing is behind the estimated breathing, the dose may be increased. If the amplitude of the patient's breathing is larger than the programmed TTSPs, then the treatment may be skipped for that region. If the amplitude of the patient's breathing is lower than the programmed TTSPs, then the dose rate may be increased for this region in order to skip this region quickly.

The general adjustment of the control signals for a lead variable of the treatment apparatus, such as the dose rate, in order to compensate for deviations of actual (or treatment) tumor position signal and the planned (or estimated) tumor position signal by detecting the difference between those signals at a given time and adjusting the control signal in accordance with that difference is conventional in the art of machine control, and is well known to those of skill in the art. Particular methods and algorithms for compensating movement of a treatment target in a patient are disclosed in Published International Patent Application No. WO 2006/113323, the entire disclosure of which is incorporated herein by reference.

Figure 6:
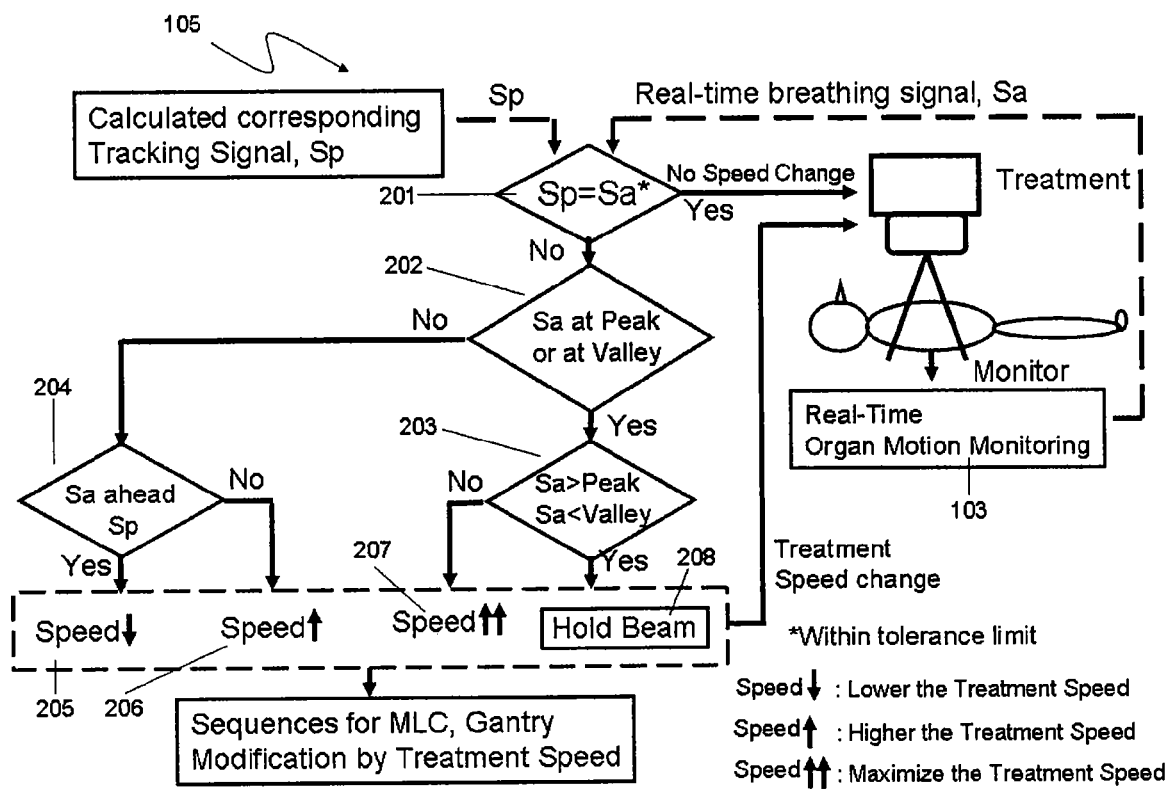
FIG. 6 illustrates a flowchart of an algorithm to a TSR Tracking embodiment.

FIG. 6 illustrates a flowchart of an algorithm to a TSR Tracking embodiment. In operation 105, the TSR Tracking compares the tracking signal, which is the equivalent breathing signal corresponding to the actual treatment delivery, with the actual breathing signal of the patient acquired by the motion monitoring unit 103. If the expected tracking signal is equal to the actual breathing signal, then no change of treatment speed is necessary and the patient is irradiated by executing the planned dynamic sequence using the current delivery speed. If not, in operation 202, the tracking processor determines if the real-time breathing (Sa) is at the peak or at the valley of the breathing pattern. If not, treatment speed will be decreased (205) when Sa is ahead (204) of the calculated corresponding signal (Sp). In operation 206, the treatment speed will be increased if Sa is behind. In operation 201 and 202, where Sa and Sp are different and Sa is in the valley or at the peak, the beam hold signal will be activated when the amplitude of the Sa is greater than that of the Sp, in operation 208. In operation 207, the treatment speed will be maximized, when the amplitude of the Sa is smaller than that of the Sp.

Figure 7:
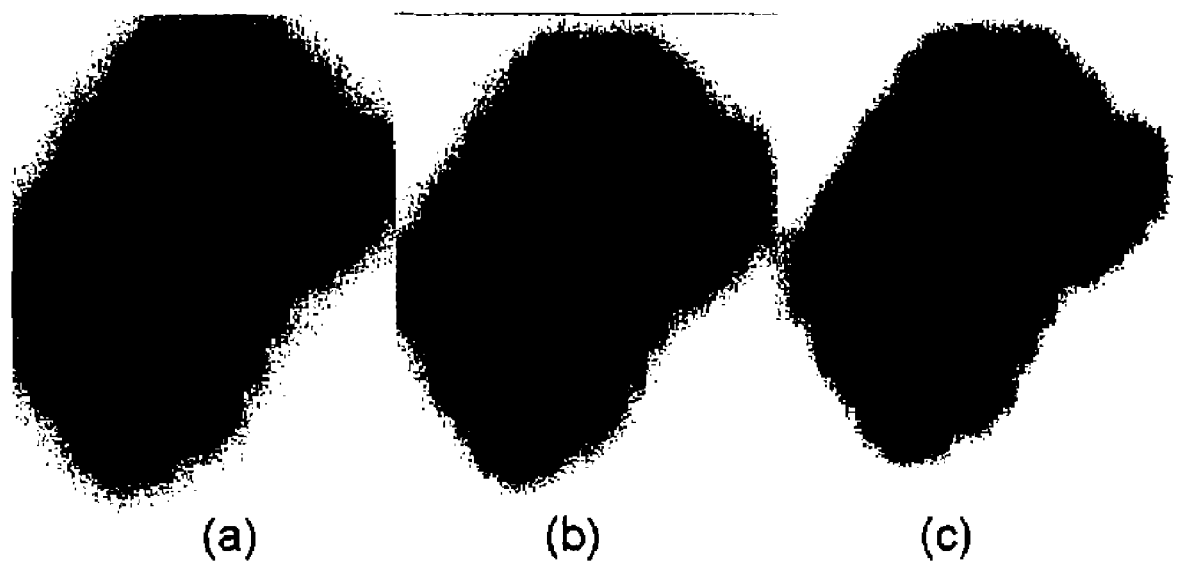
FIGS. 7A, 7B, and 7C show the results of moving phantom experiments delivering an intensity-modulated radiotherapy (IMRT) field. Films were exposed to IMRT fields with TSR Tracking and without TSR Tracking for an irregularly moving phantom.
Figure 8:
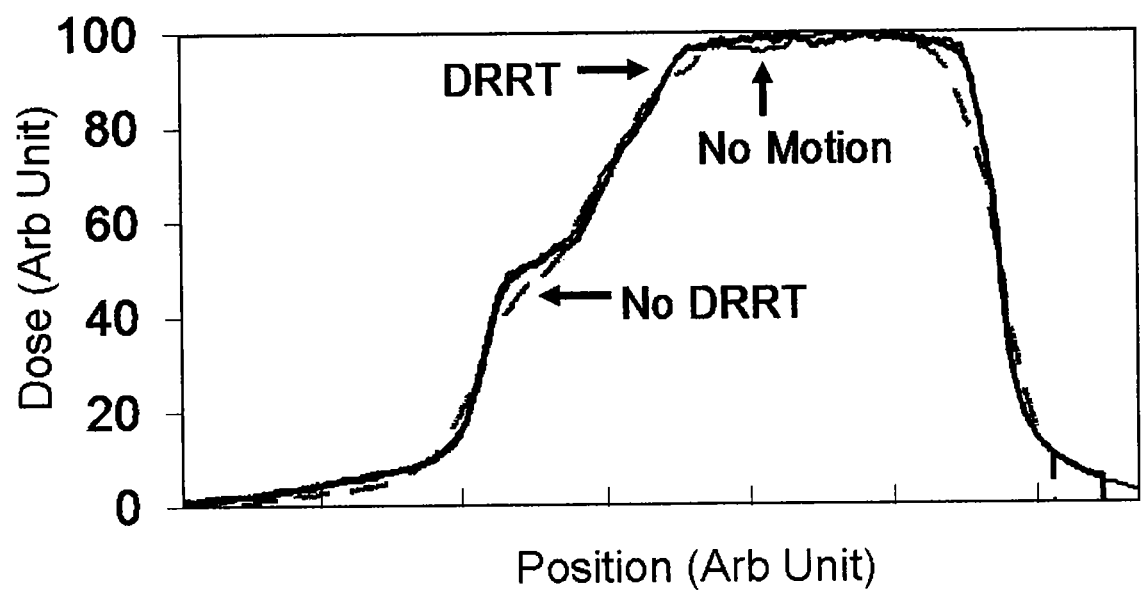
FIG. 8 shows the dose profiles of IMRT fields with and without TSR Tracking as shown in FIG. 7. The dose profiles with a step & shoot field and no phantom motion is shown as the thin solid line; that with no TSR Tracking and with irregular motion is shown as the dotted line; and the one using TSR Tracking with the same pattern of irregular motion is shown as the thick solid line.

FIGS. 7A, 7B, and 7C show the results of moving phantom experiments delivering an intensity-modulated radiotherapy (IMRT) field. Films were exposed to IMRT fields with TSR Tracking and without TSR Tracking for an irregularly moving phantom. FIG. 7A depicts a film for a static IMRT with a stationary phantom. FIG. 7B depicts a film on a moving phantom which keeps changing its frequency irregularly. FIG. 7C depicts a film on the irregularly moving phantom using TSR Tracking. FIG. 8 shows the dose profiles of IMRT fields with and without TSR Tracking as shown in FIGS. 7A, 7B, and 7C. The dose profiles with a step & shoot field and no phantom motion is shown as the thin solid line; that with no TSR Tracking and with irregular motion is shown as the dotted line; and the one using TSR Tracking with the same pattern of irregular motion is shown as the thick solid line.

While the present invention has been described in connection with the illustrated embodiments, it will be appreciated and understood that modifications may be made without departing from the spirit and scope of the invention.

What is claimed is:

1. A method for delivering therapeutic radiation during a radiation treatment procedure to a tumor moving within a patient due to physiological activity of said patient, comprising:

in a preliminary procedure, monitoring motion of said tumor in location and shape over a time period corresponding to said radiation treatment procedure, generating a surrogate signal representing said motion of said tumor, and recording said signal in a recording device to provide an estimated surrogate signal;

determining a radiation therapy plan for the patient, wherein the radiation therapy plan defines a planned sequence of varying parameters of a radiation beam to track the tumor motion and a planned rate of execution of said sequence of parameters;

configuring a radiation therapy device to deliver radiation in accordance with the radiation therapy plan;

positioning the patient within said radiation therapy device;

activating the radiation therapy device to perform said planned sequence of parameters of said radiation beam;

monitoring tumor motion during said radiation therapy procedure to provide a treatment surrogate signal;

determining the difference between said estimated surrogate signal and said treatment surrogate signal; and regulating the speed of said radiation treatment procedure by varying the rate of execution of said sequence of radiation beam parameters in accordance with said difference between said estimated surrogate signal and said treatment surrogate signal.

2. The method of claim 1 wherein said parameters of the radiation beam include at least one of dose rate, dose accumulation rate, radiation energy, rate of variation of said radiation energy, configuration of a mechanical or electronic range modulator (RM) for a charged particle beam, individual leaf positions of a multi-leaf collimator, positions of a group of leaves of the multi-leaf collimator, position and orientation of the multi-leaf collimator carriage, size and shape of a radiation field defined by an opening of the multi-leaf collimator, gantry angle, gantry speed, collimator angle or position and orientation of a patient-supporting table.

3. The method of claim 1, wherein said rate of execution of said sequence of radiation beam parameters is regulated by regulating a value of a leading control variable of said radiation therapy device.

4. The method of claim 3, wherein said leading variable is a value of delivered monitor units of radiation.

5. The method of claim 4, wherein the dose rate is regulated by regulating a pulse rate at which the radiation therapy device delivers pulses of radiation to the patient.

6. The method of claim 4, wherein the dose rate is regulated by periodically gating said radiation therapy device.

7. The method of claim 4, wherein the dose rate is regulated by regulating a pulse width at which the radiation therapy device delivers pulses of radiation to the patient.

8. The method of claim 3, wherein said leading variable is a dose rate of said radiation.

9. The method of claim 1, wherein said radiation therapy device is a megavoltage electron accelerator, a charged particle accelerator, or a radionuclide radiation device.

10. The method of claim 1, wherein said speed of said radiation treatment procedure is regulated to achieve synchrony between said estimated surrogate signal and said treatment surrogate signal at least within a within a time period that is short with respect to one breathing cycle of said patient.

11. The method of claim 1, wherein an initial portion of said treatment surrogate signal is extrapolated to serve as an estimated surrogate signal for subsequent portions of said radiation therapy treatment procedure.

12. A system for regulating the speed of radiation therapy treatment delivered to a patient by a radiation therapy device, comprising:

a detection mechanism for obtaining the time course of tumor motion (shape and location change) and its correlation with a measurable surrogate, typically a physical signal associated with breathing or the location of implanted markers in the tumor, for a patient in need of radiation therapy;

a determining mechanism for determining a radiation therapy plan for the patient, the radiation therapy plan including a target location that varies in accordance with the estimated breathing pattern;

a configuring mechanism for configuring the radiation therapy device to deliver radiation in accordance with the radiation therapy plan;

an activating mechanism for activating the radiation therapy device;

a monitoring mechanism for monitoring an actual breathing pattern of the patient during delivery of radiation;

a second determining mechanism for determining a difference between the estimated breathing pattern and the actual breathing pattern of the patient; and a regulating mechanism for regulating a treatment speed of the radiation therapy device in accordance with the difference.

13. The system of claim 12, wherein the dose rate is regulated by regulating a pulse rate at which the radiation therapy device delivers pulses of radiation to the patient.

14. The system of claim 12, wherein the dose rate is regulated by regulating a pulse width at which the radiation therapy device delivers pulses of radiation to the patient.

15. The system of claim 12, wherein the radiation therapy device is mounted on a moving gantry, said moving gantry moving at a specified gantry speed, and the gantry speed is regulated by a mechanical breaker.

16. The system of claim 15, wherein the radiation therapy device is provided with a multi-leaf collimator, a dose rate of said radiation therapy is regulated by moving leaves of said multi-leaf collimator under control of said configuring mechanism, and said moving gantry may assume angular positions during said radiation therapy deviating from planned angular positions of said gantry by a predetermined amount.

17. The system of claim 16, wherein said gantry may assume angular positions during said radiation treatment deviating from said planned angular oppositions by an amount not exceeding about 5 degrees of arc.

18. The system of claim 12, wherein a rate of change of a dose rate of said radiation therapy is regulated by providing gating signals to said radiation therapy device.

19. The system of claim 12, wherein said radiation therapy device includes a charged particle beam having a mechanical range modulator and said modulator is controlled by regulating a pulse rate thereof.

20. The system of claim 12, wherein said radiation therapy device includes a charged particle beam having a mechanical range modulator and said modulator is controlled by regulating a pulse width thereof.

21. The system of claim 12, wherein said radiation therapy device includes a charged particle beam having a digital range modulator and said modulator is controlled by regulating a pulse rate thereof.

22. The system of claim 12, wherein said radiation therapy device includes a charged particle beam having a mechanical range modulator and said modulator is controlled by regulating a pulse width thereof.

23. The system of claim 12, wherein said determining mechanism for determining a radiation therapy plan for the patient, determines a radiation therapy plan for a target that moves throughout an estimated range of motion of a tissue to be treated.

* * * * *